(12) United States Patent
Ahari

(10) Patent No.: US 10,166,084 B2
(45) Date of Patent: Jan. 1, 2019

(54) SPRING-EJECTED BIOPSY MARKER

(71) Applicant: DEVICOR MEDICAL PRODUCTS, INC., Cincinnati, OH (US)

(72) Inventor: Frederick Ahari, Belleair Beach, FL (US)

(73) Assignee: Devicor Medical Products, Inc., Cincinnati, OH (US)

( * ) Notice: Subject to any disclaimer, the term of this patent is extended or adjusted under 35 U.S.C. 154(b) by 1053 days.

(21) Appl. No.: 14/534,952

(22) Filed: Nov. 6, 2014

(65) Prior Publication Data

US 2016/0128784 A1    May 12, 2016

(51) Int. Cl.
*A61B 90/00* (2016.01)
*A61M 37/00* (2006.01)
*A61B 17/34* (2006.01)

(52) U.S. Cl.
CPC .......... *A61B 90/39* (2016.02); *A61B 17/3468* (2013.01); *A61B 2090/3904* (2016.02); *A61B 2090/3987* (2016.02); *A61M 37/0069* (2013.01)

(58) Field of Classification Search
CPC ................ A61B 90/39; A61B 17/3468; A61B 2090/3904; A61B 2090/3987; A61M 37/0069
See application file for complete search history.

(56) References Cited

U.S. PATENT DOCUMENTS

| | | | |
|---|---|---|---|
| 6,220,248 B1 | 4/2001 | Voegele et al. | |
| 6,261,302 B1 * | 7/2001 | Voegele | A61B 90/39 606/142 |
| 7,625,397 B2 | 12/2009 | Foerster et al. | |
| 8,068,895 B2 * | 11/2011 | Speeg | A61B 90/39 600/431 |
| 8,079,964 B2 * | 12/2011 | Reichel | A61B 90/39 424/1.25 |
| 8,556,931 B2 * | 10/2013 | Franco | A61B 8/0833 606/213 |
| 9,108,026 B2 * | 8/2015 | Deckard | A61B 17/22012 |

(Continued)

FOREIGN PATENT DOCUMENTS

WO    WO 2007/069105 A2    6/2007

OTHER PUBLICATIONS

Written Opinion of related International Application No. PCT/US2015/059563 dated Sep. 30, 2016.

(Continued)

*Primary Examiner* — Angela M Hoffa
(74) *Attorney, Agent, or Firm* — Frost Brown Todd LLC

(57) ABSTRACT

A tool for inserting a marker into tissue at a biopsy site includes an elongate plunger having a blind bore. A plunger rod has a proximal end received within and secured to the blind bore so that the plunger rod moves conjointly with the plunger and a spring is secured to the distal end of the plunger rod. A cannula has a lumen that receives a distal end of the plunger rod and a crimp is formed in the cannula near its distal end. The cannula has a side exit port where a marker is ejected from the lumen. A ramp is formed in communication with the side exit port and the ramp has a preselected slope that controls the angle at which the marker is ejected. The marker is ejected from the side exit port into tissue when the spring unloads abruptly as the marker clears the crimp.

6 Claims, 10 Drawing Sheets

(56) References Cited

U.S. PATENT DOCUMENTS

| | | | |
|---|---|---|---|
| 2006/0167416 A1* | 7/2006 | Mathis | A61B 10/0275 604/164.01 |
| 2007/0142725 A1* | 6/2007 | Hardin | A61B 90/39 600/431 |
| 2008/0119881 A1 | 5/2008 | Vetter | |
| 2009/0156929 A1* | 6/2009 | Franco | A61B 8/0833 600/424 |
| 2009/0209804 A1* | 8/2009 | Seiler | A61B 17/3468 600/7 |
| 2009/0216150 A1* | 8/2009 | Reichel | A61B 90/39 600/562 |
| 2009/0216181 A1* | 8/2009 | Speeg | A61B 90/39 604/60 |
| 2010/0063345 A1 | 3/2010 | Yuasa | |
| 2011/0071423 A1 | 3/2011 | Speeg et al. | |
| 2012/0165789 A1* | 6/2012 | Deckard | A61B 17/22 604/528 |
| 2013/0006101 A1 | 1/2013 | Mchugo et al. | |
| 2014/0243844 A1 | 8/2014 | Clancy et al. | |
| 2015/0360019 A1* | 12/2015 | Clancy | A61B 90/39 600/432 |
| 2017/0231716 A1* | 8/2017 | Ahari | A61B 90/39 600/431 |

OTHER PUBLICATIONS

International Search Report and Written Opinion of Internation Application No. PCT/US2015/059563 dated Mar. 30, 2016.

* cited by examiner

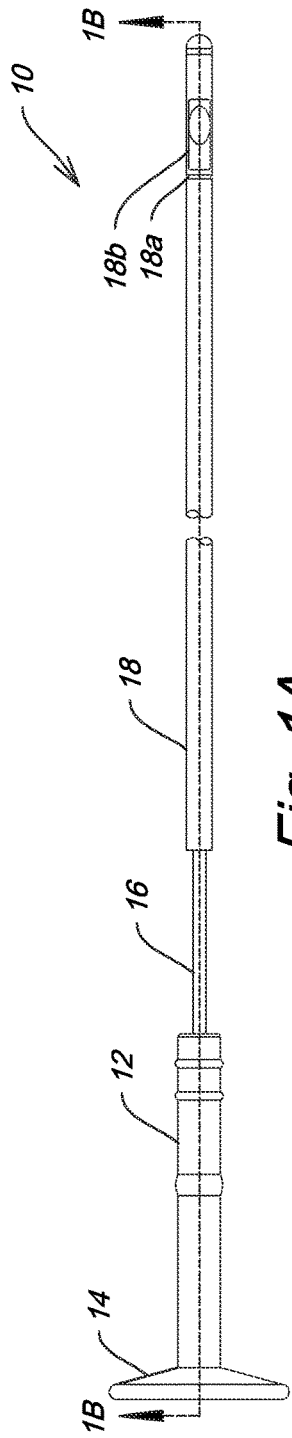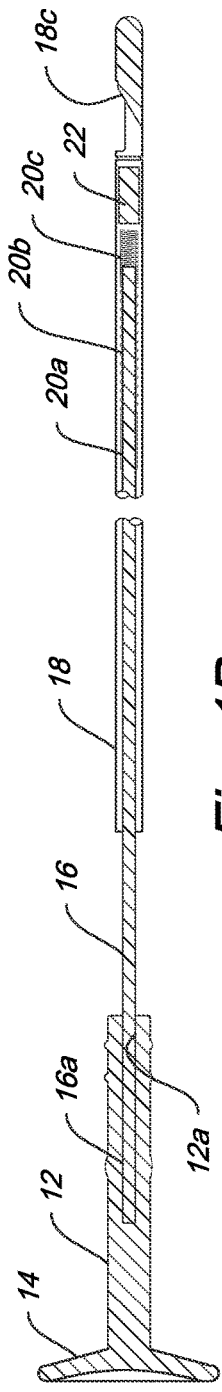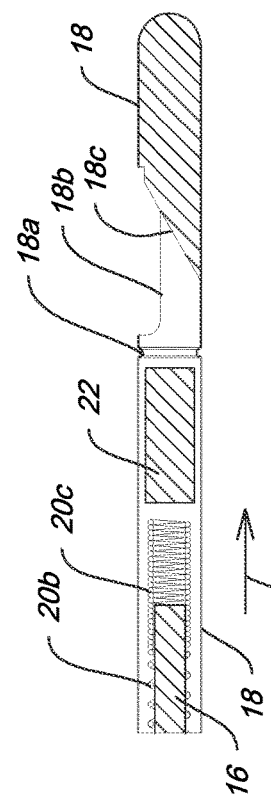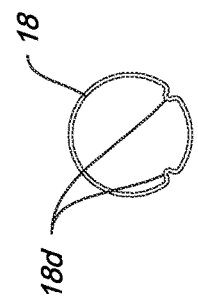
Fig. 1A
Fig. 1B
Fig. 1C
Fig. 1D

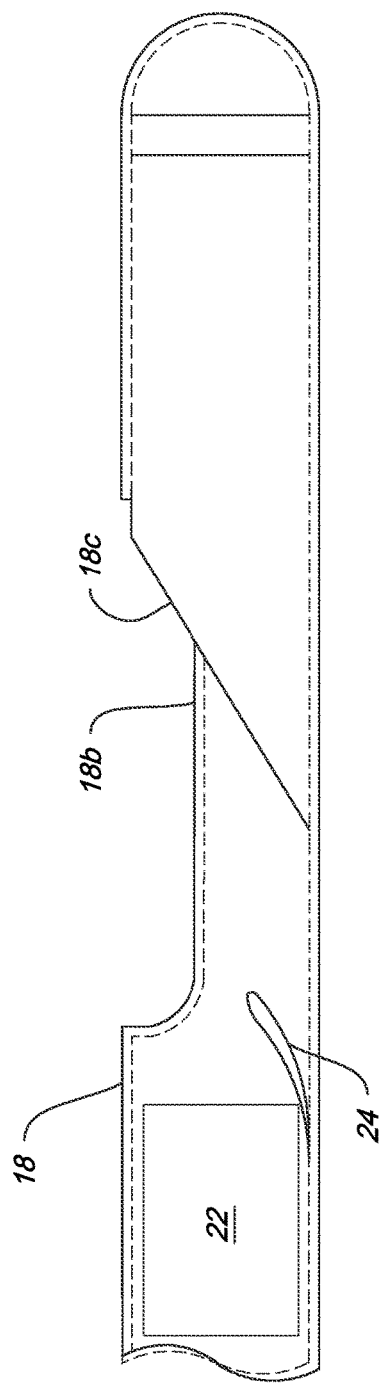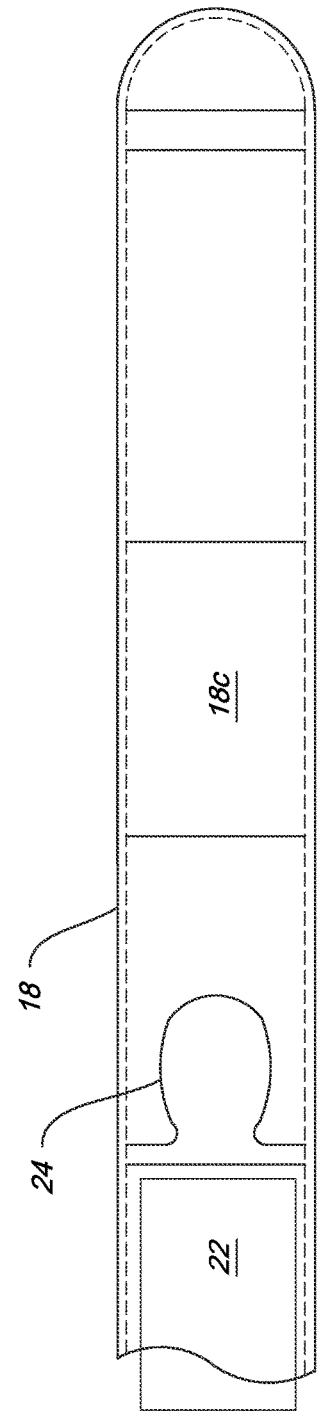

SPRING-EJECTED BIOPSY MARKER

BACKGROUND OF THE INVENTION

1. Field of the Invention

This invention relates, generally, to devices that insert biopsy markers at biopsy sites.

More particularly, it relates to a device that employs a spring to eject a marker into tissue from a side port of the device.

2. Description of the Prior Art

Devices that eject biopsy markers from a side exit port are well-known. An example of such a device is disclosed in U.S. Pat. No. 7,625,397 and an earlier example is disclosed in U.S. Pat. No. 6,220,248.

The primary drawback of the earlier devices is that said devices provide no means for controlling the amount of force used to eject the marker. Thus, the power applied to the marker to eject it is determined by the amount of force applied by the physician and such force may vary for each procedure, even for the same physician. Thus, some markers are ejected with greater force than others and thus the placement of the marker relative to the desired position will vary.

Thus there is a need for a device that ejects the marker with the same amount of force each time it is used. Such a device would operate independently of any force applied by a user and would ensure a uniform, repeatable placement of the marker.

However, in view of the art considered as a whole at the time of making the present invention, how to provide the needed apparatus was not obvious to those of ordinary skill in the art.

SUMMARY OF THE INVENTION

The long-standing but heretofore unfulfilled need for a device that enables consistent placement of a marker at a biopsy site is now met by a new, useful, and non-obvious invention.

The novel tool includes an elongate plunger having a blind bore. A plunger rod has a proximal end received within and secured to the blind bore so that it moves conjointly with the plunger. An elongate cannula having a lumen slidingly receives a distal end of the plunger rod.

An annular crimp is formed in the cannula near its distal end and a side exit port is formed in the cannula distal of the annular crimp. The marker is ejected from the lumen into a patient's tissue only after it fully clears the annular crimp. A ramp is formed in communication with the side exit port and has a preselected slope that controls the angle at which the marker is ejected from the lumen.

A spring is secured to the distal end of the plunger rod. A detent formed on the plunger rod abuts the proximal end of the spring so that proximal-to-distal displacement of the plunger rod causes compression of the spring.

In a first embodiment, the novel method includes the steps of forming a biopsy site marker of a material that is sufficiently compressible and resilient to enable it to squeeze without permanent deformation through an opening having a diameter less than the diameter of the marker. A blind bore is formed in an elongate plunger and a proximal end of a plunger rod is secured in the blind bore so that the plunger rod moves conjointly with the plunger. A spring is secured to the distal end of the plunger rod and a detent is formed on the plunger rod on the proximal side of the spring so that proximal-to-distal movement of the plunger rod compresses the spring.

A distal end of the plunger rod is inserted into the lumen of an elongate cannula. An annular crimp is formed in the cannula near its distal end, and a side exit port is formed in the cannula where the marker is ejected from the lumen. The side exit port is distal of the annular crimp. A ramp is formed in communication with the side exit port and has a preselected slope that controls the angle at which the marker is ejected from the lumen.

In an alternative embodiment, the annular crimp is replaced by two to eight (2-8) circumferentially spaced apart dimples. The dimples perform the same function as the annular crimp.

The marker is initially positioned within the lumen of the cannula in closely spaced apart distal relation to the spring and in closely spaced apart proximal relation to the annular crimp.

The plunger rod is then displaced in a proximal-to-distal direction until the leading end of the spring abuttingly engages the marker but does not displace the marker. The plunger rod is then further displaced in the proximal-to-distal direction until its leading end is flush with the leading end of the spring. Further displacement of the plunger rod in the same direction drives the marker at least in part through the annular crimp or the dimples and at least in part up the ramp.

Still further displacement of the plunger rod in the proximal-to-distal direction causes the plunger rod to push the marker further through the annular crimp or dimples and further up the ramp. The leading end of the plunger rod is now positioned flush with a plane transverse to the proximal edge of the annular crimp or dimples and the proximal end of the marker is the only part of the marker in the grip of the annular crimp or dimples.

The plunger rod is then displaced further in the same direction until the proximal end of the marker clears the crimp. The spring unloads abruptly as its potential energy changes into kinetic energy and that kinetic energy drives the marker up said ramp and ejects it into tissue through the side exit port at an angle determined by the angle of the ramp.

A second method for inserting a marker into tissue at a biopsy site includes the steps of forming a biopsy site marker of a rigid material that is neither compressible nor resilient. As in the first embodiment, a blind bore is formed in an elongate plunger and a proximal end of a plunger rod is received within and secured to the blind bore so that the plunger rod moves conjointly with the plunger.

A distal end of the plunger rod is inserted into the lumen of an elongate cannula. A spring is secured to the distal end of the plunger rod and a detent is formed on the plunger rod. The detent abuts the proximal end of the spring so that proximal-to-distal travel of the plunger rod causes compression of the spring.

A flap is formed in the cannula that extends into a lumen of the cannula at a predetermined angle near a distal end of the cannula. The flap provides resistance to proximal-to-distal travel of the marker.

A side exit port is formed in the cannula where the marker is ejected from the lumen, said side exit port being positioned distal of the flap. The side exit port includes a ramp having a preselected slope that controls the angle at which the marker is ejected from the lumen.

The marker is positioned within the lumen of the cannula in closely spaced apart distal relation to the spring and in closely spaced apart proximal relation to the flap.

The plunger rod is displaced in a proximal-to-distal direction until the leading end of the spring abuttingly engages the marker but does not displace the marker.

The plunge rod is then further displaced in the same direction until the leading end of the plunger rod is flush with the leading end of the spring and therefore abuts the proximal end of the marker.

Continued displacement of the plunger rod in the same direction drives the marker at least in part past the flap and at least in part up the ramp. Still further same direction displacement causes the plunger rod to push the marker past the flap and further up the ramp so that the leading end of the plunger rod is positioned flush with a plane transverse to the proximal end of the flap and the proximal end of the marker is the only part of the marker in contact with the flap.

Still further same direction displacement of the plunger rod causes the proximal end of the marker to clear the flap. The spring unloads abruptly as its potential energy changes into kinetic energy and that energy ejects the marker up the ramp and into tissue at an angle determined by the angle of the ramp.

A third embodiment replaces the annular crimp or dimples of the first embodiment and the flap of the second embodiment with a detent that does not encircle the cannula. However, it performs the same function performed by said annular crimp/dimples and said flap, i.e., it provides a steady resistance to marker displacement that a physician can feel and it provides such steady resistance up to the moment that the detent is cleared and the marker is launched up the ramp and into tissue by the abrupt unloading of the spring.

An important object of this invention is to provide a means for placing a biopsy marker in tissue that in a consistent, repeatable way.

Another important object is to provide a tool that gives palpable feedback to a surgeon when pushing a biopsy site marker through the lumen of a cannula.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which:

FIG. 1A is a side elevation view of the novel structure including a broken-away part to indicate that the length of the structure may be any preselected length;

FIG. 1B is a longitudinal sectional view taken along line 1B-1B in FIG. 1A;

FIG. 1C is an enlarged view of the distal end of the structure depicted in FIG. 1B;

FIG. 1D depicts an alternative embodiment where dimples replace the annular crimp of the first embodiment;

FIG. 3B is a longitudinal, side elevation sectional view of the structure depicted in FIG. 3A;

FIG. 3C is a longitudinal, top plan sectional view of the structure depicted in FIG. 3A.

DETAILED DESCRIPTION OF THE PREFERRED EMBODIMENT

Figure 2A:
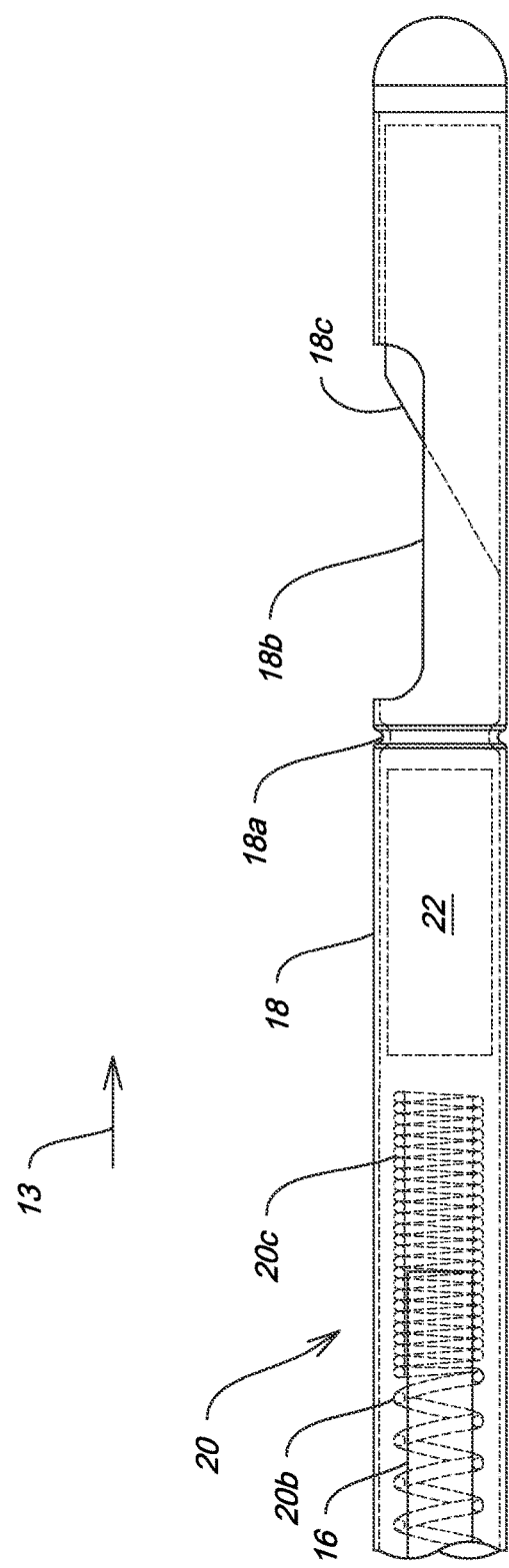
FIG. 2A is the first drawing of a series of six side elevation drawings providing an animation of the operation of the novel structure.

The reference numeral 10 in FIG. 1A denotes an illustrative embodiment of the novel structure as a whole.

Tool 10 includes plunger 12 having an enlarged proximal end 14 which serves as a handle for the user. Proximal end 16a (FIG. 1B) of elongate plunger rod 16 is received within bore 12a formed with plunger 12 and is secured thereto so that plunger rod 16 moves conjointly with plunger 12.

Elongate cannula 18 slidingly receives the distal end of plunger rod 16. Annular crimp 18a, best depicted in FIG. 1C, is formed in cannula 18 near its distal end. A side exit port where a marker 22 is ejected from the lumen of cannula 18 is denoted 18b. The slope of ramp 18c controls the angle at which marker 22 is ejected from the lumen of cannula 18.

As depicted in FIGS. 1B and 1C, spring 20 is secured to the distal end of plunger 16. In FIG. 1C, marker 22 is positioned within the lumen of cannula 18 in closely spaced apart distal relation to spring 20 and in closely spaced apart proximal relation to annular crimp 18a. Annular detent 20a (FIG. 1B) is a weld formed integrally with plunger 16 and secures the proximal end of spring 20 to said plunger 16 so that said spring does not slide with respect to said plunger.

Spring 20 is preferably a coil spring and its coils are spaced apart from one another at the proximal end thereof as indicated by reference numeral 20b. The coils are tightly packed relative to one another at the distal end of spring 20 as indicated by reference numeral 20c.

Accordingly, displacement of plunger 12 in a proximal-to-distal direction as indicated by reference numeral 13 in FIG. 1C causes the leading (distal) end of plunger 12 to abuttingly engage marker 22 but does not displace said marker past annular crimp 18a until loosely packed coils 20b have become tightly packed. Continued displacement of plunger 16 in said proximal-to-distal direction after loosely packed coils 20b are tightly packed forces marker 22 through annular crimp 18a.

An alternative structure to annular crimp 18a is depicted in FIG. 1D. In the depicted example, two (2) circumferentially spaced apart dimples, collectively denoted 18d, are formed in cannula 18 at the same longitudinal position that is occupied by annular crimp 18a in the original embodiment. Defining the top of cannula 18 in FIG. 1D as being the zero degree (0°) position, a first dimple is positioned approximately at the one hundred thirty five degree (135°) position and the second dimple is positioned approximately at the two hundred twenty five degree (225°) position. Each dimple 18d has the same depth as annular crimp 18a. Any number of such dimples are within the scope of this invention, it being understood that annular crimp 18a could be formed by a large number of closely spaced dimples. However, the preferred number of equidistantly, circumferentially spaced apart dimples is as few as two (2) as depicted to as many as eight (8). If eight (8) dimples are selected, there is one (1) dimple at the zero degree (0°) position and one dimple every forty five degrees (45°) thereafter about the circumference of cannula 18.

FIG. 2A is substantially the same as FIG. 1C. No force is applied to plunger 16. Spring 20 is therefore in repose so that coils 20b are spaced apart from one another and coils 20c are tightly packed with respect to one another. Marker 22 is also in repose on the proximal side of annular crimp 18a or dimples 18d.

Figure 2B:
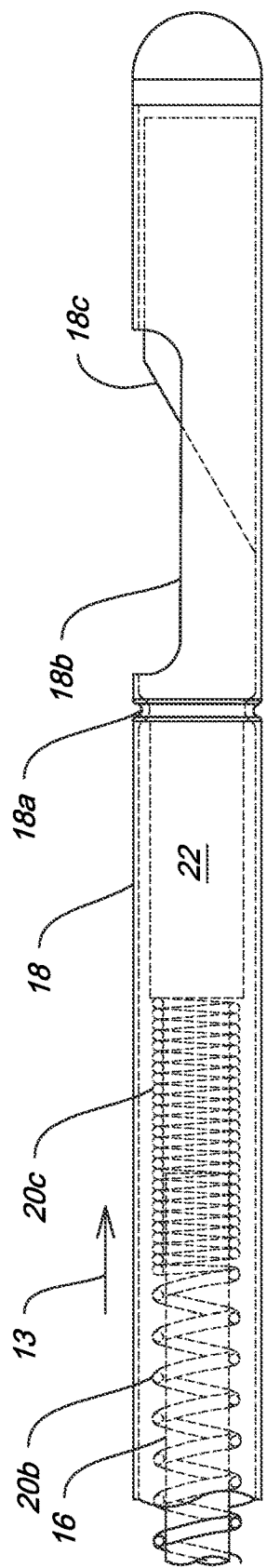
FIG. 2B is the second drawing of said series.

As best understood by comparing FIGS. 2A and 2B with one another, FIG. 2B depicts plunger 16 displaced in proximal-to-distal direction 13 from its in-repose position of FIG. 2A. Loosely packed coils 20b remain loosely packed but the leading end of tightly packed coils 20c now abuttingly engages marker 22 which remains on the proximal side of annular crimp 18a or dimples 18d.

Figure 2C:
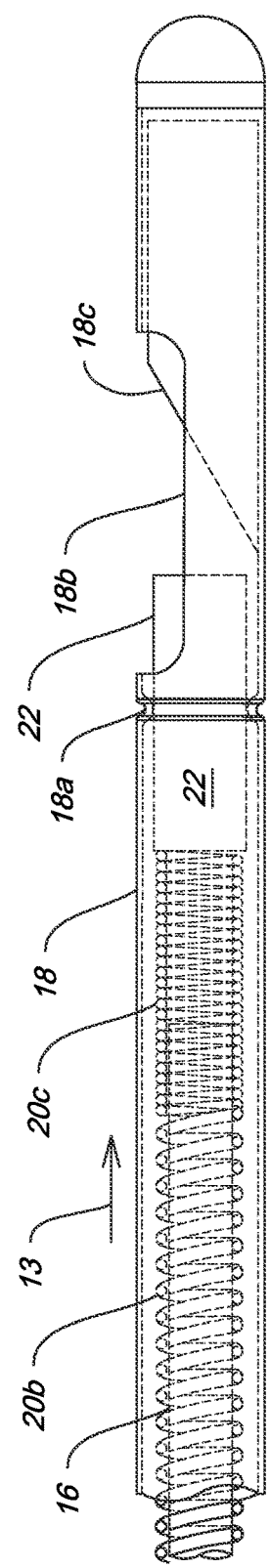
FIG. 2C is the third drawing of said series.

As depicted in FIG. 2C, continued displacement of plunger 16 in proximal-to-distal direction 13 causes tightly packed coils 20c to begin pushing marker 22 through annular crimp 18a or dimples 18d. Marker 22 is made of a material that is sufficiently compressible and resilient to enable it to be squeezed without permanent deformation through an opening having a diameter less than the diameter of the marker. The leading end of plunder 16 is spaced apart from marker 22 as depicted.

Figure 2D:
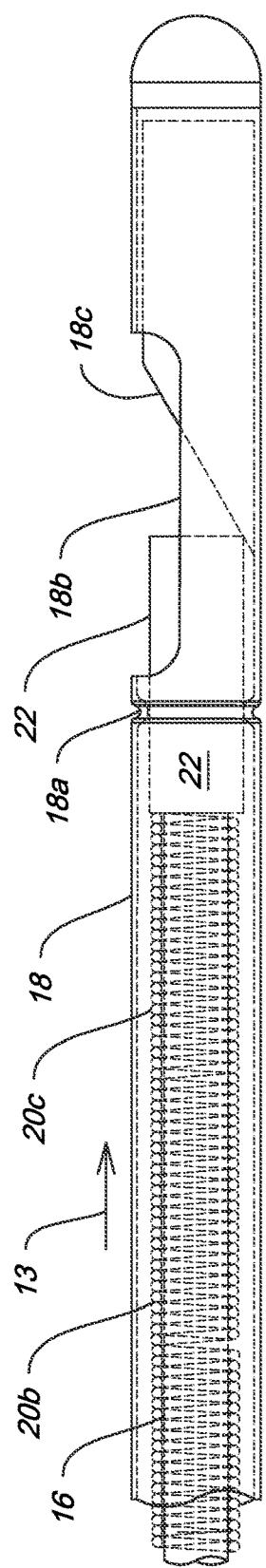
FIG. 2D is the fourth drawing of said series.

As depicted in FIG. 2D, still further displacement of plunger 16 in said proximal-to-distal direction 13 brings the leading (distal) end of plunger 16 into abutting engagement with marker 22. Thus, the leading end of plunger 16 is flush with the leading end of spring 20. The resistance to marker 22 displacement provided by annular crimp 18a or dimples 18d is greater than the resistance provided by tightly packed coils 20c to displacement of plunger 16 in said proximal-to-distal direction 13. Accordingly, coils 20b are also now tightly packed as depicted. The leading end of plunger 16 and the trailing end of marker 22 are both on the proximal side of annular crimp 18a as depicted.

Figure 2E:
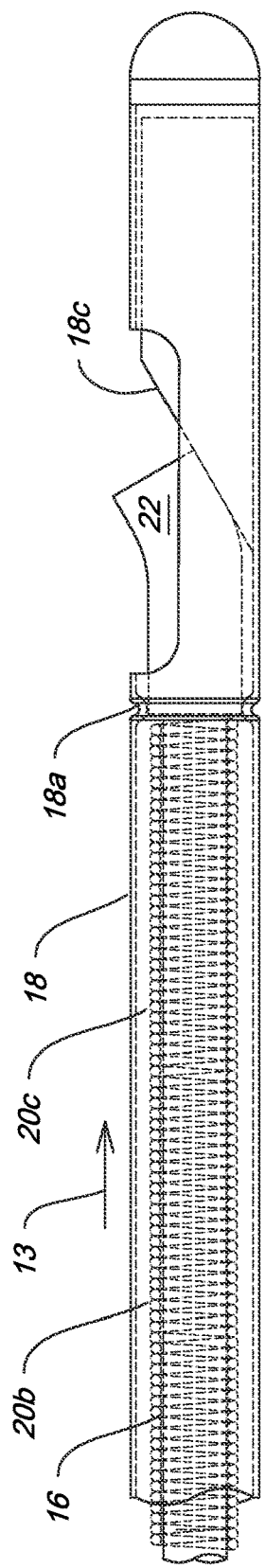
FIG. 2E is the fifth drawing of said series.

As depicted in FIG. 2E, still further displacement of plunger 16 in said proximal-to-distal direction 13 drives marker 22 up ramp 18c. The leading end of plunger 16 is now positioned flush with a plane transverse to the proximal/trailing edge of annular crimp 18a as depicted and the proximal/trailing end of marker 22 is the only part of marker 22 in the grip of said annular crimp 18a or dimples 18d.

Figure 2F:
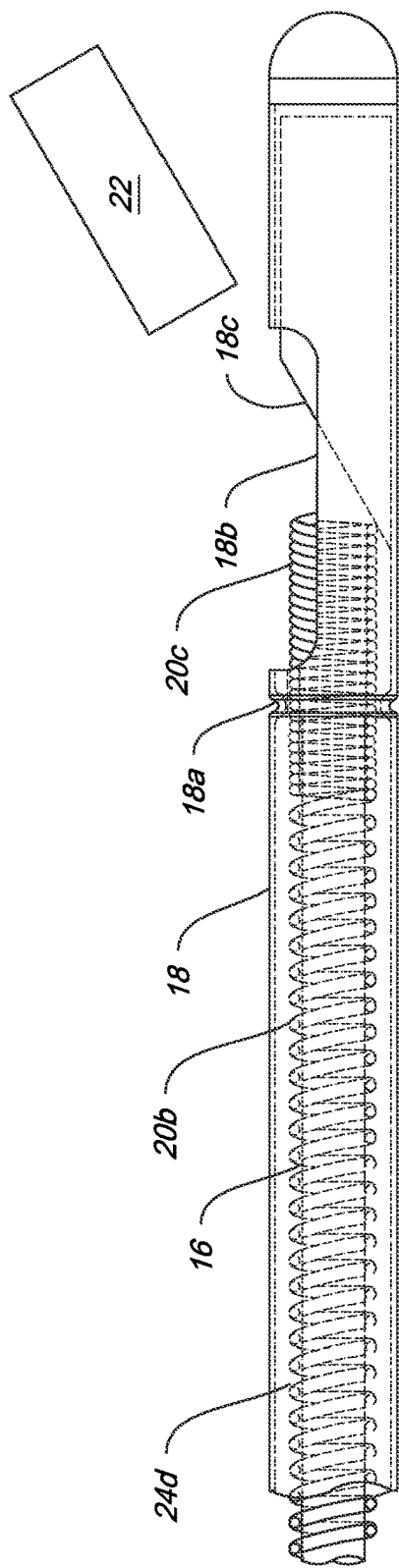
FIG. 2F is the sixth drawing of said series.

FIG. 2F depicts marker 22 after it ejection into tissue at an angle determined by the angle of ramp 18c. Comparison of FIGS. 2E and 2F indicates that plunger 16 is displaced in proximal-to-distal direction 13 from its FIG. 2E position to its FIG. 2F position. Such displacement pushes the leading end of plunger 16 past annular crimp 18a or dimples 18d so that the trailing end of marker 22 clears said annular crimp 18a or dimples 18d. Marker 22 therefore provides no further resistance to spring 20 so the potential energy stored in spring 20 is converted instantaneously into kinetic energy, assuming its FIG. 2F position and ejecting marker 22 through side exit port 18b into said tissue. Coils 20b therefore return to their loosely packed configuration as depicted. This sudden release of potential energy is reproduced every time the novel apparatus is used, thereby accomplishing the primary object of the invention.

The resilience of the material that forms marker 22 enables its leading end to bend upwardly to conform to the angle of ramp 18c while its trailing end remains unbent, and further allows marker 22 to regain its undeformed cylindrical shape after it is no longer engaged by said ramp.

Figure 3A:
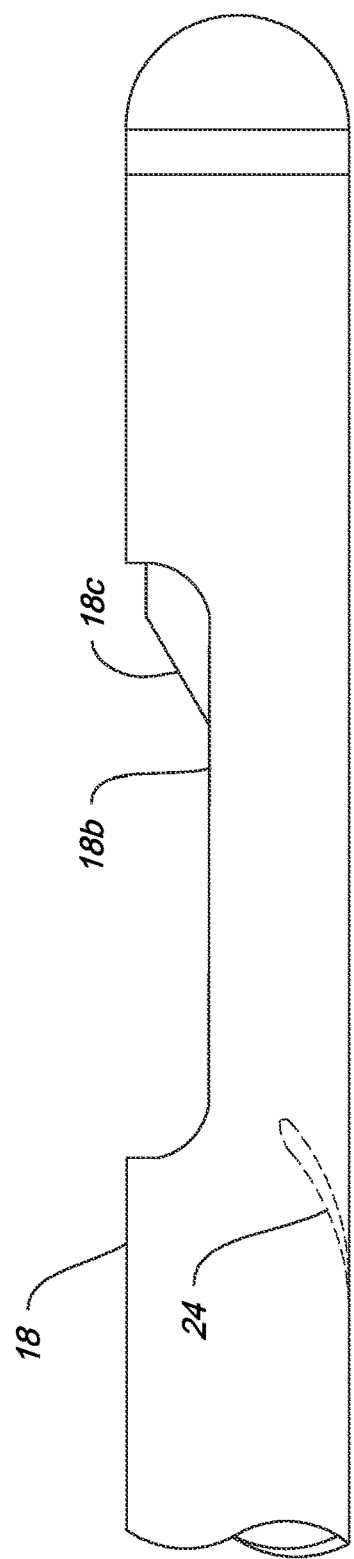
FIG. 3A diagrammatically depicts a second embodiment in side elevation.

FIGS. 3A-C depict a second embodiment. This embodiment eliminates annular crimp 18a as well as dimples 18d. Flap 24 is hidden from view in the side elevation view of FIG. 3A, and is visible in the longitudinal, side elevation sectional view of FIG. 3B and the longitudinal, top plan sectional view of FIG. 3C. Flap 24 and cannula 18 are formed integrally with one another and said flap provides the detent that resists proximal-to-distal displacement of marker 22 by plunger 16, i.e., flap 24 performs the same function as annular crimp 18a or dimples 18d, resisting unloading of spring 20 until plunger 16 pushes the trailing end of marker 22 past said flap, at which time spring 20 unloads substantially instantaneously as in the first embodiment. This second embodiment is employed when marker 22 is formed of a material that is not flexible and resilient.

Figure 4:
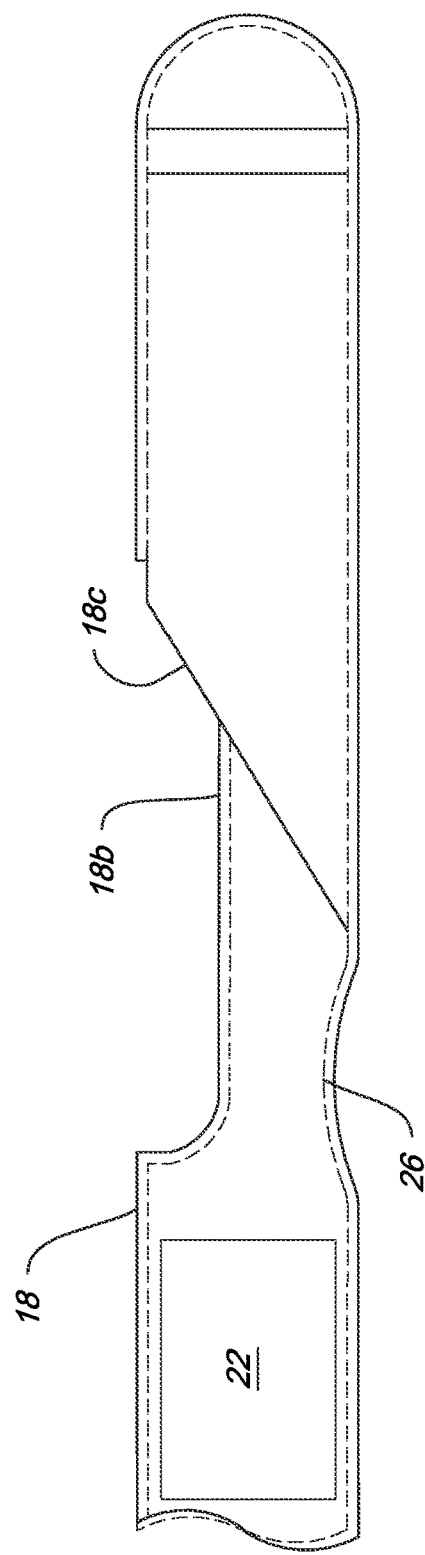
FIG. 4 is a side elevation view of a third embodiment.

FIG. 4 depicts a third embodiment. Like the second embodiment, it is used with rigid marker 22. A protuberance or bulge 26 is formed in the lumen of cannula 18 and said bulge performs the same function as flap 24 of the second embodiment, i.e., bulge 26 flattens as rigid marker 22 is pushed over it.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A tool for inserting a marker into tissue at a biopsy site, comprising:
    an elongate plunger having a blind bore formed therein;
    a plunger rod having a proximal end received within and secured to said blind bore so that said plunger rod moves conjointly with said plunger;
    an elongate cannula having a lumen that receives a distal end of said plunger rod;
    a stop formed on an inner surface of said cannula near a distal end of said cannula;
    said cannula having a side exit port where said marker is ejected from said lumen of said cannula;
    said side exit port being positioned distal of said stop;
    a ramp formed in communication with said side exit port, said ramp having a preselected slope that controls the angle at which said marker is ejected from said lumen;
    a spring secured to said distal end of said plunger rod and extending axially relative to said plunger rod along a longitudinal axis defined by the plunger rod; and
    said plunger rod attached to the proximal end of said spring so that
proximal-to-distal displacement of said plunger rod causes compression of said spring between said plunger rod and said marker to thereby force the marker past the stop via the spring.

2. The tool of claim 1, wherein said stop is an annular crimp.

3. The tool of claim 1, wherein said stop is formed by at least two dimples formed in said cannula.

4. The tool of claim 3, wherein said at least two dimples are disposed in equidistantly and circumferentially spaced relation to one another.

5. The tool of claim 4, wherein said at least two dimples includes two dimples spaced about ninety degrees from one another.

6. The tool of claim 3, wherein said at least two dimples includes between two to eight dimples.

\* \* \* \* \*